United States Patent [19]

Terni et al.

[11] Patent Number: 4,910,196

[45] Date of Patent: Mar. 20, 1990

[54] HIGHLY SOLUBLE ANTIBACTERIALLY ACTIVE ORGANIC SALTS OF PYRIDOBENZOTHIAZINES

[75] Inventors: Patrizia Terni; Pier L. Rugarli; Stefano Maiorana, all of Milan; Pier G. Pagella, Isola S. Antonio; Raffaello Fusco, Milan, all of Italy

[73] Assignee: Mediolanum Farmaceutici Srl, Italy

[21] Appl. No.: 64,460

[22] Filed: Jun. 22, 1987

[30] Foreign Application Priority Data

Jul. 1, 1986 [IT] Italy .................... 20997 A/86

[51] Int. Cl.$^4$ .................... A61K 31/54; C07D 513/04
[52] U.S. Cl. .................... 514/224.5; 544/32
[58] Field of Search ............ 544/32; 514/222, 224.5

[56] References Cited

U.S. PATENT DOCUMENTS 4,668,784 5/1987 Mascellani et al. ................... 544/32

OTHER PUBLICATIONS

Mediolanum Farmaceutiti, Chemical Abstracts, vol. 104:207290f (1986).
Otsuka Pharm., Chemical Abstracts, vol. 101:151868u (1984).
Daiichi Seiyaku, Chemical Abstracts, vol. 98:198294p (1983).
Fravolini et al., Chemical Abstracts, vol. 105:218250q (1985).
Cecchetti et al., Chemical Abstracts, vol. 106:102,235e (1987).

Primary Examiner—John M. Ford
Attorney, Agent, or Firm—Arnold, White & Durkee

[57] ABSTRACT

New highly soluble antibacterially active salts of pyridobenzothiazines with organic acids are described. In particular, organic salts of 9-fluoro-10[N-(4'-methyl)-piperazinyl]-7-oxo-2,3-dihydro-7H-pyrido[1,2,3][1,4]-benzothiazine-6-carboxylic acid are prepared with an acid chosen from the group consisting of methanesulphonic acid, ethanesulphonic acid, n-dodecanesulphonic acid, p-toluenesulphonic acid, 1-actadecanesulphonic acid, 2-chloro-ethanesulphonic acid, 2-bromo-ethanesulphonic acid, 3-hydroxy-propanesulphonic acid, citric acid, malonic acid, gluconic acid, malic acid, lactic acid and L-tartaric acid.

A new process is also described for preparing said salts from 2,3,4-trichloronitrobenzene, by way of a 2-fluoro-3-chloro-4-mercapto derivative of the nitrobenzene and cyclizing the corresponding amino derivative.

6 Claims, No Drawings

HIGHLY SOLUBLE ANTIBACTERIALLY ACTIVE ORGANIC SALTS OF PYRIDOBENZOTHIAZINES

This invention relates to new highly soluble antibacterially active salts of pyrido-benzothiazines with organic acids.

More precisely, the invention relates to organic salts of 9-fluoro-10[N-(4'-methyl)piperazinyl]-7-oxo-2,3-dihydro-7H-pyrido[1,2,3de][1,4]benzothiazine-6-carboxylic acid with an organic acid chosen from the group consisting of methanesulphonic acid, ethanesulphonic acid, n-dodecanesulphonic acid, p.toluenesulphonic acid, 1-octadecanesulphonic acid, 2-chloroethanesulphonic acid, 2-bromo-ethanesulphonic acid, 3-hydroxy-propanesulphonic acid, citric acid, malonic acid, gluconic acid, malic acid, lactic acid and L-tartaric acid.

It has been surprisingly found that the new salts according to the present invention are much more soluble in water than the corresponding pyrido-benzothiazine hydrochlorides prepared up to the present time, and some of them demonstrate, when in solution, pH values more compatible with human use in collyria, ointments and solutions for parenteral use.

In this respect, whereas the water solubility of the hydrochloride is generally between 5 and 20 mg/ml, the solubility for example of the corresponding sulphonates is between 80 and 100 mg/ml and that of the corresponding gluconates is between 350 and 400 mg/ml.

In particular, the solubility of the hydrochloride of 9-fluoro-10[N-(4'-methyl)piperazinyl]-7-oxo-2,3-dihydro-7H-pyrido[1,2,3 de][1,4]benzothiazine-6-carboxylic acid in water is 8 mg/ml, whereas the solubility of the corresponding methanesulphonate is 87 mg/ml, with a pH of approximately 3, the solubility of the corresponding gluconate being 360 mg/ml with a pH of about 5.

The antibacterial activity of the salts according to the present invention is in no way modified by their salification with organic acids. This considerable solubility increase coupled with the favourable pH value enables these medicaments to be administered not only orally but also parenterally and topically, by dissolving the effective antibacterial dose in a small volume of vehicle.

In particular, the preparation of these medicaments for parenteral use in small vials is a great advantage in terms both of the local and psychological toleration of the patient, and of the size of their confections.

Parenteral therapy is very useful in the case of patients affected by gastrointestinal disturbance, and in the case of hospitalised patients. The particularly high pH of certain salts, such as the gluconic acid salt, enables them to also be used in special formulations as collyria and ointments.

The pyrido-benzothiazine salts according to the present invention are prepared by dissolving the pyrido-benzothiazine, and in particular 9-fluoro-10[N-(4'-methyl)piperazinyl]-7-oxo-2,3-dihydro-7H-pyrido[1,2,3 de][1,4]benzothiazine-6-carboxylic acid, in suitable solvents such as chlorobenzene, toluene, xylene or water, and reacting the solution with an equimolar quantity of an organic acid such as methanesulphonic acid, ethanesulphonic acid, n-dodecanesulphonic acid, p.toluenesulphonic acid, 1-octadecanesulphonic acid, 2-chloroethanesulphonic acid, 2-bromo-ethanesulphonic acid, 3-hydroxy-propanesulphonic acid, citric acid, malonic acid, gluconic acid, malic acid, lactic acid and L-tartaric acid.

Processes for preparing pyrido-benzothiazines, which are the starting substance for the new salts claimed herein, have been described in a previous patent of the present applicant (European patent application 85101881.2). The described processes all pass through a key intermediate, namely 7-fluoro-8-chloro-3,4-dihydro-2H-1,4-benzothiazine (III).

We have now discovered a new process, forming a further subject of the present invention, which enables said intermediate (III) to be prepared with particularly high yields, to thus allow the new salts according to the invention to be obtained more conveniently on an industrial scale.

It is however apparent that the new pyrido-benzothiazine salts can also be prepared by preparing the intermediate by known processes.

A second subject of the present invention is therefore a process for preparing pyrido-benzothiazines of formula

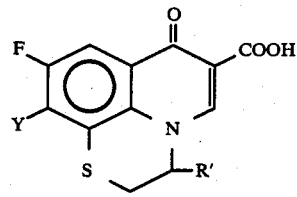

in which Y is a nitrogenated cyclic base radical of 5 or 6 atoms, and R' is H or $C_1$–$C_6$ alkyl, and in particular a new process which enables the compound of formula

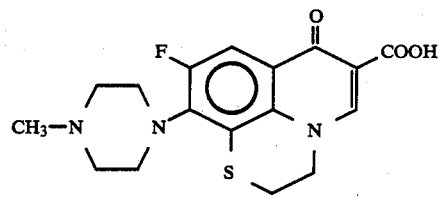

or its salts with organic acids to be prepared in an industrially economical manner by way of the intermediate of formula

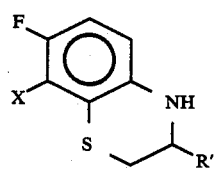

in which X is halogen and R' is as heretofore defined.

The intermediate of formula (III) is prepared in an industrially economical manner essentially starting from 2,3,4-trichloronitrobenzene, by cyclisation of a 2-fluoro-3-chloro-4-mercapto derivative of the aminobenzene prepared from it.

Schematically the new process can be represented as follows:

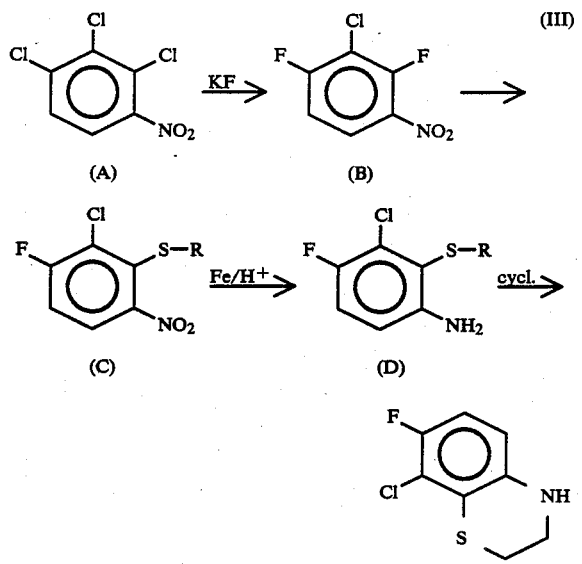

in which R is H, —CH$_2$—COOET, —CH$_2$—CH$_2$—OH or —CH$_2$—CH$_2$Br.

The key passage of this process is the preparation of 2,4-difluoro-3-chloronitrobenzene (B) from 2,3,4-trichloronitrobenzene, a compound available industrially at low cost.

The 2,3,4-trichloronitrobenzene, easily obtainable by nitrating the 1,2,3-trichlorobenzene, is reacted with dried KF in DMF or DMSO at a temperature of about 150° C., to give 2,4-fluoro-3-chloro-nitrobenzene (B). From this, according to a first alternative comprising reaction with Na$_2$S.9H$_2$O at a temperature of between 20° and 50° C. in a stream of N$_2$, 2-mercapto-3-chloro-4-fluoro-nitrobenzene is obtained, this being a compound (C$_1$) in which R is H.

This compound is dissolved at ambient temperature in a dipolar aprotic solvent such as DMF or DMSO, ethyl chloroacetate is added and the mixture allowed to react for 2–3 hours at ambient temperature to give ethyl 2-chloro-3-fluoro-6-nitrobenzenethioglycolate, a compound (C$_2$) in which R is —CH$_2$—CH$_2$—COOET.

The same product can also be obtained directly from the 2,4-difluoro-3-chloronitrobenzene (B) by reaction with ethyl thioglycolate in DMF at ambient temperature. The thioether (C$_2$) is then reduced and simultaneously cyclised to give 7-fluoro-8-chloro-2H-1,4-benzothiazin-3(4H)-one. The reaction is conducted in acetic acid in the presence of concentrated HCl, using Fe powder as reducing agent, this being added slowly to the mixture in such a manner that the temperature does not rise above 35° C.

The benzothiazinone is reduced to benzothiazine preferably by means of metal hydrides such as AlH$_3$, LiAlH$_4$, NaBH$_4$ and the like in a suitable organic solvent at ambient temperature.

According to an alternative procedure, the 2,4-fluoro-3-chloronitrobenzene (B) is reacted with mercaptoethanol under controlled conditions to arrive at the formulation of 3-chloro-4-fluoro-2-(2-hydroxyethyl)mercaptonitrobenzene (C$_3$), which by reduction with iron in hydrochloric acid forms 3-chloro-4-fluoro-2-(2-hydroxyethyl)mercaptoaniline (D$_1$). From this latter, by nucleophilic substitution of the hydrobromic acid, 3-chloro-4-fluoro-2-(2-bromoethyl)mercaptoaniline (D$_2$) is obtained which, by heating with soda in ethanol, cyclises to 8-chloro-7-fluoro-3,4-dihydro-2H-1,4-benzothiazine (III).

In both cases the benzothiazine obtained is purified by dissolving in an organic solvent and precipitating as the hydrochloride with gaseous HCl.

The process for preparing the key intermediate when carried out in this manner gives an overall yield of 40%, compared with a maximum yield of 25% obtained by the previously described process (a) and a maximum yield of 20% obtained by the previously described process (b) (European patent application 85101881.2).

The further steps of the process up to the preparation of the pyrido-benzothiazines of formula (I) are conducted in accordance with the scheme given hereinafter, in which the intermediate (III) is converted in a single passage into the acid (IV) which, by oxidation to the corresponding sulphoxide, nucleophilic substitution with YH amines and reduction, gives the compounds (I).

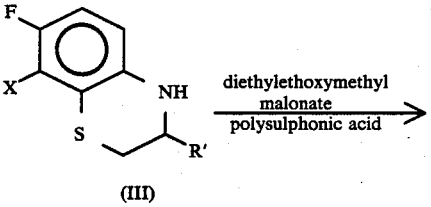

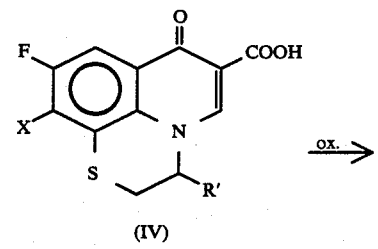

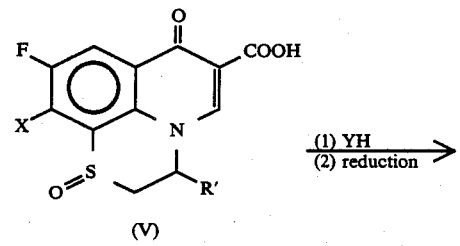

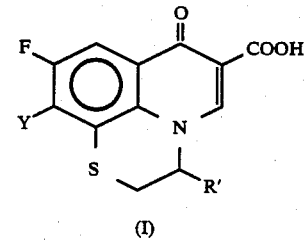

The operating conditions are described in detail in Example 3.

The pyrido-benzothiazines obtained in this manner, and in particular 9-fluoro-10[N-(4'-methyl)piperazinyl]-7-oxo-2,3-dihydro-7H-pyrido[1,2,3 de][1,4]benzothiazine-6-carboxylic acid (II), are dissolved in a suitable organic solvent, preferably chosen from the group consisting of chlorobenzene, toluene and xylene, and are reacted with an equimolar quantity of an organic sulphonic acid of formula RSO₃H, preferably chosen from the group consisting of methanesulphonic acid, ethanesulphonic acid, n-dodecanesulphonic acid, p.toluenesulphonic acid, 1-octadecanesulphonic acid, 2-chloroethanesulphonic acid, 2-bromoethanesulphonic acid and 3-hydroxy-propanesulphonic acid, or a carboxylic acid preferably chosen from the group consisting of citric acid, malonic acid, gluconic acid, malic acid, lactic acid and tartaric acid.

Some practical preparation examples are given hereinafter by way of non-limiting illustration only, in order to allow the new salts according to the invention to be more easily reproduced.

EXAMPLE 1

Preparation of 7-fluoro-8-chloro-3,4-dihydro-2H-1,4-benzothiazine

A—Preparation of

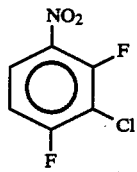
(B)

30 g (0.132 moles) of 2,3,4-trichloronitrobenzene (A) are dissolved in 100 ml of DMF, 23 g (0.39 moles) of potassium fluoride are added, and the mixture allowed to react for 16 hours at 150° C.

Chromatography (benzene/hexane 3/7) is used to check when the reaction has terminated, after which water is added and the mixture distilled with steam. The distillate is extracted with CH₂Cl₂ to obtain 19.5 g of a yellowy solid. Yield 75%. M.P. 44°–46° C.

B—Preparation of

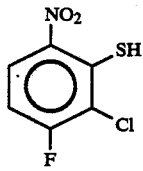
(C₁)

16.84 g (0.0758 moles) of sodium sulphide nonahydrate are added in portions, over a period of about 30–40 minutes, to 13.47 g (0.07 moles) of compound (B) dissolved in 65 cc of DMF and kept under an N₂ stream, the temperature being maintained at about 20°–25° C.

When the addition is complete, the mixture is left under agitation at ambient temperature for about 1 hour to enable the reaction to go to completion.

The mixture is poured into iced water, acidified with 2N HCl to about pH 3, and the solid obtained is filtered off and well squeezed. 12.3 g are obtained with a yield of 85%.

The product is used without further purification for the next reaction. A portion of solid is purified by silica gel chromatography using benzene/AcOH 8/2 as eluent to obtain a yellowy semisolid with the following characteristics:

IR (nujol): 2.560 cm⁻¹ (νS—H), 11.335 and 1.570 cm⁻¹ (νN=O);

¹H-NMR (CDCl₃-TMS) δ ppm: 5.28 (1H, s, S—H), 7.05 (1H, m, C₅—H), 8.2 (1H, m, C₆—H).

C—Preparation of

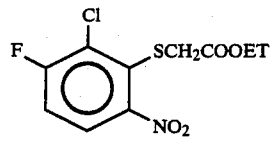
(C₂)

5 g (0.024 moles) of compound (C₁) are dissolved at ambient temperature in 100 cc of DMF under magnetic agitation, and 28 ml (0.027 moles) of ethyl chloroacetate are added.

The mixture is left under agitation at ambient temperature, the progress of the reaction being checked by TCL (petroleum ether/ethyl acetate 85/15) on samples withdrawn at predetermined time intervals. After 3 hours the starting compound has completely disappeared.

The mixture is poured into water, extracted with CH₂Cl₂ and the organic extract washed several times with water.

The methylene chloride is dried over Na₂SO₄, filtered and evaporated to obtain 5.1 g of crude product which is used unpurified in the next reaction.

¹H-NMR (CDCl₃-TMS) δ ppm: 1.2 (3H, t, OCH₂CH₃), 3.73 (2H, s, —S—CH₂), 4.15 (2H, q, O—CH₂), 7.32 (1H, m, C₅—H), 7.65 (1H, m, C₆—H).

Alternatively:

2 g (0.01 moles) of compound (B) are dissolved in 20 cc of DMF, 1.2 ml (0.011 moles) of ethyl thioglycolate are added, and the mixture allowed to react at ambient temperature for 3 hours.

On termination the mixture is poured into water and extracted with CH₂Cl₂ to obtain 2.2 g of product (C₂) in mixture with a small quantity of para-substituted isomer.

D—Preparation of

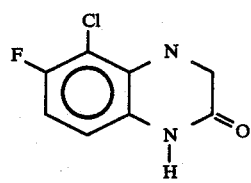
(E)

0.05 g (0.0017 moles) of compound (C₂) are dissolved in 3.5 ml of glacial acetic acid and 0.17 ml of 36% hydrochloric acid are added.

While maintaining the mixture under magnetic agitation, 400 mg (0.007 moles) of powdered iron are added in portions, the addition being regulated in such a manner that the temperature does not rise above 35° C. When the addition is complete, the mixture is left at ambient temperature for 2 hours and then filtered through celite to remove any iron residues, and washed well with cold water, hot water and finally with chloroform.

After separation, the organic phase is dried over Na₂SO₄, filtered and the solvent evaporated.

In this case the intermediate compound (D) is not isolated, but instead 310 mg of pure product (E) are obtained directly with a yield of 83.66%. M.P. 193°–196° C.

E—Preparation of

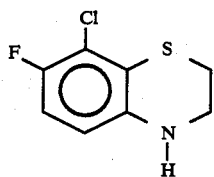 (III)

165 mg (0.00076 moles) of compound (E) are suspended in 30 ml of anhydrous THF and subjected to magnetic agitation. 0.033 g (0.0009 moles) of LiAlH$_4$ are added in portions and the mixture left at ambient temperature for 2 hours. On termination of the reaction small quantities of methanol are added to destroy the hydride, followed by water. The mixture is extracted with chloroform, the organic phase washed with water, dried over Na$_2$SO$_4$, and the solvent evaporated.

125 mg of a yellowy oil are obtained, equivalent to a yield of 80%.

$^1$H-NMR (CDCl$_3$-TMS) δ ppm: 3.0 (2H, m, —CH$_2$—N), 3.45 (2H, m, CH$_2$—S), 3.8 (1H, s, N—H), 6.15 (1H, m, C$_5$—H), 6.52 (1H, m, C$_6$—H).

EXAMPLE 2

Second method for preparing 7-fluoro-8-chloro-3,4-dihydro-2H-1,4-benzothiazine (III)

F—Preparation of

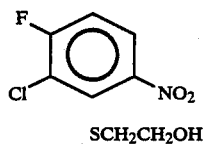 (C$_3$)

117 g (0.6 moles) of compound (B) and 46.8 g (0.6 moles) of mercaptoethanol are added to 300 ml of ethanol, the solution cooled to 0° C. and 87 ml (0.63 moles) of triethylamine dripped slowly in, maintaining the temperature around 0° C. On termination of the addition the mixture is left under agitation at that temperature for about 1 hour (TLC check, CH$_2$Cl$_2$/AcOEt 9/1), the solvent evaporated, the product taken up in water and extracted with methylene chloride. 145 g of a yellow-orange oil are obtained from the organic phase after drying and evaporation. Yield 96%.

$^1$H-NMR (CDCl$_3$-TMS) δ ppm: 2.43 (1H, t, O—H), 3.15 (2H, m, CH$_2$OH), 3.75 (2H, m, S—CH$_2$), 7.21 (1H, m, C$_5$—H), 7.59 (1H, m, C$_6$—H).

IR (film): 1.360 and 1.530 cm$^{-1}$ (νN=O).

G—Preparation of

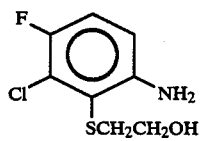 (D$_1$)

145 g (0.578 moles) of compound (F) are dissolved in 300 ml of ethanol, and 430 cc of 30% HCl are gradually added in such a manner that the mixture temperature reaches 40°–45° C. 97 g (1.73 g.atom) of powdered iron are added in portions while maintaining the temperature around this value. On completion of the addition, the mixture is left under agitation for about 30 minutes and the termination of the reaction checked by TLC (CH$_2$Cl$_2$/AcOEt 9/1). The small quantity of unreacted iron is then filtered off, the ethanol evaporated under vacuum and 70 g (0.85 moles) of sodium acetate in water added. This operation results in the separation of an oil, which is extracted with CH$_2$Cl2. 128 g (quantitative yield) of an oily residue having the following characteristics are obtained from the organic phase after drying and evaporation:

$^1$H-NMR (CDCl$_3$-TMS) δ ppm: 2.93 (2H, m, CH$_2$OH), 3.60 (2H, m, S—CH$_2$), 4.00 (3H, s, NH$_2$ and OH), 6.58 (1H, m, C$_6$—H), 6.93 (1H, m, C$_5$—H).

IR (film): bands due to the nitro group disappear.

H—Preparation of

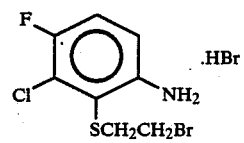 (D$_2$)

128 g (0.578 moles) of compound (D$_1$) are suspended in 320 ml of 47% HBr and heated to about 120° C. for 4–5 hours. On termination of the reaction (TLC check with toluene/AcOEt 2/1), about 300 ml of HBr are distilled off under reduced pressure to obtain 300 g of residue containing aniline hydrobromide, which is used as such for the next reaction.

L—Preparation of

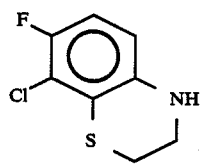 (III)

300 g of product (D$_2$) suspended in 300 ml of ethanol are heated to 50°–60° C. until completely dissolved, and concentrated NaOH is added until alkaline pH persists. The mixture is heated to 70°–75° C. for about 2 hours, the ethanol evaporated under vacuum and the product extracted with CH$_2$Cl$_2$. 95 g are obtained (yield 80% over two passages) of a browny oil which shows the same characteristics as the product obtained in Example 1.

EXAMPLE 3

Preparation of 10-chloro-9-fluoro-7-oxo-2,3-dihydro-7H-pyrido[1,2,3 de][1,4]benzothiazine-6-carboxylic acid 15.8 g of product (III) are treated with 19 ml of ethyl ethoxymethylenemalonate at 120° C. under agitation for 1.5 hours.

55 g of polyphosphoric acid are then added, the mixture raised to a temperature of 160° C. and kept at this temperature for 1 hour. On termination it is allowed to cool to 120° C., water is added, and the mixture allowed to react for about 1 hour at a temperature of about 100° C. while keeping it continuously under agitation.

It is cooled and the solid formed is filtered off, and washed well with water.

18.6 g of a whitish solid are obtained with a yield of 80%.

$^1$H-NMR (CF$_3$COOH-TMS) δ ppm: 3.68 (2H, m, N—CH$_2$), 5.28 (2H, m, S—CH$_2$), 8.22 (1H, d, C$_8$—H, J$_{H\text{-}F}$≈8 Hz), 9.40 (1H, s, C$_5$—H).

IR (nujol): 3.070 cm$^{-1}$ (C—H), 1.718 cm$^{-1}$ (C=O).
U.V. (EtOH) λ$_{max}$ 253, 341 μm.
M.P. 311°–313° C.

Preparation of
10-chloro-9-fluoro-7-oxo-2,3-dihydro-7H-pyrido[1,2,3 de][1,4]benzothiazine-1-oxido-6-carboxylic acid 15 g of the intermediate obtained heretofore are suspended in 400 cc of AcOH and 6.7 cc of 33% H$_2$O$_2$ diluted in 100 cc of AcOH are added. The mixture is allowed to react at 50° C. for 20 hours, on termination of which it is cooled and the insoluble solid filtered off.

14 g of a whitish solid are obtained, equivalent to a yield of 90%.

M.P. 294°–298° C.

$^1$H-NMR (CF$_3$COOH-TMS) δ ppm: 8.74 (1H, d, C$_8$—H, J$_{H\text{-}F}$≈7 Hz), 9.7 (1H, s, C$_5$—H).

IR (nujol): 1.049 cm$^{-1}$, 1.029 cm$^{-1}$.

UV (EtOH) λ$_{max}$ 224, 270, 354 μm.

Preparation of
9-fluoro-10[N-(4′-methyl)piperazinyl]-7-oxo-2,3-dihydro-7H-pyrido[1,2,3 de][1,4]benzothiazine-6-carboxylic acid hydrochloride 16 cc of methyl piperazine are added to 6.5 g of the aforesaid sulphoxide suspended in 100 cc of DMF, the temperature is raised to 100°–105° C. to obtain complete dissolution, and the solution kept under agitation for 45 minutes at 90°–95° C.

The solvent is evaporated and the residue taken up in ethanol to provide 9-fluoro-10[N-(4′-methyl)-piperazinyl]-7-oxo-2,3-dihydro-7H-pyrido[1,2,3 de][1,4]benzothiazine-1-oxido-6-carboxylic acid with a yield of 82%.

$^1$H-NMR (CF$_3$COOH-TMS) δ ppm: 3.3 (3H, d, N—CH$_3$), 3.9 (10H, m, N—H$_2$), 5.4 (2H, m, S—CH$_2$), 8.77 (1H, d, C$_8$—H, J$_{H\text{-}F}$≈10.5 Hz), 9.68 (1H, s, C$_5$—H).

Percentage analysis: Theoretical: C 53.82%; H 4.78%; N 11.07%. Found: C 53.34%; H 4.65; N 10.82%.

This latter product can then be reduced to finally obtain compound (II). 5 g of the compound obtained as described are suspended in 250 cc of DMF, the solution cooled to 0°–5° C. with an ice and salt bath and 4 cc of PCl$_3$ dripped slowly in. The mixture is allowed to react cold for 15 minutes, 150 cc of water are then added to extinguish the excess of PCl$_3$, and the mixture kept under agitation at ambient temperature for about 1 hour.

The solvent is evaporated, the residue taken up in EtOH and the insoluble solid obtained is filtered off to give a yield of 93%.

The 9-fluoro-10[N-(4′-methyl)piperazinyl]-7-oxo-2,3-dihydro-7H-pyrido[1,2,3 de][1,4]benzothiazine-6-carboxylic acid hydrochloride can be crystallised under hot conditions from a mixture of EtOH/H$_2$O in the proportion 7/3.

M.P. 315°–320° C.

$^1$H-NMR (CF$_3$COOH-TMS) δ ppm: 3.2 (3H, d, N—CH$_3$), 3.8 (10H, m, N—CH$_2$), 5.15 (2H, m, CH$_2$—S), 8.18 (1H, d, C$_8$—H), J$_{H\text{-}F}$≈10.5 Hz), 9.4 (1H, s, C$_5$—H).

UV (H$_2$O) λ$_{max}$ 245 μm and 296 μm.

EXAMPLE 4

Preparation of
9-fluoro-10[N-(4′-methyl)piperazinyl]-7-oxo-2,3-dihydro-7H-pyrido[1,2,3 de][1,4]benzothiazine-6-carboxylic acid methanesulphonate 1.2 cc of methanesulphonic acid are added to 2.16 g of compound (II) suspended in 100 cc of chlorobenzene. The mixture is heated to 130° C. and left to react for 1 hour. On termination of the reaction it is cooled and the chlorobenzene decanted. The yellow oily residue is taken up in acetone to obtain 2.5 g of a yellowy solid equivalent to a yield of 91%.

The product can be crystallised from an EtOH/H$_2$O 75/25 mixture.

$^1$H-NMR (CF$_3$COOH-TMS) δ ppm: 9.38 (1H, d, C$_5$—H), 8.2 (1H, d, C$_8$—H, J$_{HF}$≈10.5 Hz), 5.12 (2H, m, S—CH$_2$), 3.7 (13H, m).

Percentage analysis: Theoretical: C 47.05%; H 4.82%; N 9.14%. Found: C 46.85%; H 4.75%; N 8.95%.

M.P. 339°–341° C.

EXAMPLE 5

Using the method described in Example 1, other derivatives were prepared, namely:

9-fluoro-10[N-(4′-methyl)piperazinyl]-7-oxo-2,3-dihydro-7H-pyrido[1,2,3 de][1,4]benzothiazine-6-carboxylic acid ethanesulphonate $^1$H-NMR (CF$_3$COOH-TMS) δ ppm: 9.35 (1H, s, C$_5$—H), 8.15 (1H, d, C$_8$—H, J$_{HF}$≈10 Hz), 5.12 (2H, m, S—CH$_2$), 3.63 (15H, m), 1.5 (3H, t, CH$_3$—CH$_2$).

Percentage analysis: Theoretical: C 48.19%; H 5.11%; N 8.87%. Found: C 47.66%; H 5.05%; N 8.72%.

M.P. 342°–344° C.

9-fluoro-10[N-(4′-methyl)piperazinyl]-7-oxo-2,3-dihydro-7H-pyrido[1,2,3 de][1,4]benzothiazine-6-carboxylic acid p.toluenesulphonate $^1$H-NMR (CF$_3$COOH-TMS) δ ppm: 9.35 (1H, s, C$_5$—H), 8.12 (1H, d, C$_8$—H, J$_{HF}$≈10.5 Hz), 7.82 (2H, d, H$_2$ and H$_6$, p-toluenesulphonic acid), 7.32 (2H, d, H$_3$ and H$_5$ p-toluenesulphonic acid), 5.12 (2H, m, S—CH$_2$), 3.60 (13H, m), 2.5 (3F, s, CH$_3$CH$_2$).

Percentage analysis: Theoretical: C 53.82%; H 4.89%; N 7.84%. Found: C 53.68%; H 4.82%; N 7.74%.

M.P. 275°–278° C.

9-fluoro-10[N-piperazinyl]-7-oxo-2,3-dihydro-7H-pyrido[1,2,3 de][1,4]benzothiazine-6-carboxylic acid methanesulphonate Percentage analysis: Theoretical: C 45.83%; H 4.52%; N 9.43%. Found: C 45.71%; H 4.48%; N 9.45%.

M.P. 343°–345° C.

9-fluoro-10[N-piperazinyl]-7-oxo-2,3-dihydro-7H-pyrido[1,2,3 de][1,4]benzothiazine-6-carboxylic acid ethanesulphonate Percentage analysis: Theoretical: C 47.05%; H 4.83%; N 9.14%. Found: C 46.90%; H 4.79%; N 9.10%.

M.P. 348°–349° C.

EXAMPLE 6

Preparation of salts of 9-fluoro-10[N-(4'-methyl)piperazinyl]-7-oxo-2,3-dihydro-7H-pyrido[1,2,3 de][1,4]benzothiazine-6-carboxylic acid with organic carboxylic acids General example:

0.5 g of 9-fluoro-10[N-(4'-methyl)piperazinyl]-7-oxo-2,3-dihydro-7H-pyrido[1,2,3 de][1,4]benzothiazine-6-carboxylic acid are suspended in 10 cc of $H_2O$, an equimolar quantity of the chosen organic acid is added, the mixture heated to 40°-50° C. for 2 hours and then left under agitation at ambient temperature overnight. On termination, the insoluble product is filtered off or the solution lyophilised.

Salt with gluconic acid
M.P. 340°-342° C.
Solubility in $H_2O$: 0.36 g/ml; pH 5.07-5.10.
Percentage analysis: Theoretical: C 49.37%; H 5.40%; N 7.51%. Found: C 49.08%; H 5.33%; N 7.36%.

Salt with malonic acid
M.P. 288°-289° C.
Solubility in $H_2O$: 3 mg/ml; pH 4.22.
Percentage analysis: Theoretical: C 52.61%; H 4.62%; N 8.76%. Found: C 52.48%; H 4.53%; N 8.46%.

Salt with citric acid
M.P. 278°-280° C.
Solubility in $H_2O$: 2.7 mg/ml; pH 3.99-4.00.
Percentage analysis: Theoretical: C 49.73%; H 4.72%; N 7.56%. Found: C 49.86%; H 4.70%; N 7.53%.

Salt with L-tartaric acid
M.P. 292°-294° C.
Solubility in $H_2O$: 6 mg/ml; pH 4.09-4.10.
Percentage analysis: Theoretical: C 49.12%; H 4.71%; N 8.18%. Found: C 49.05%; H 4.67%; N 8.10%.

The following pharmaceutical formulations were prepared:

capsules containing 25, 50, 100, 200, 300, 400 mg of 9-fluoro-10[N-(4'-methyl)piperazinyl]-7-oxo-2,3-dihydro-7H-pyrido[1,2,3 de][1,4]benzothiazine-6-carboxylic methane sulphonate with suitable diluents and excipients.

tablets containing 25, 50, 100, 200, 300, 400 mg of methanesulphonate or gluconate with suitable diluents and excipients.

vials containing 25, 50, 100, 200, 300, 400 mg of methanesulphonate or gluconate together with the required quantity of water.

collyria containing 0.05-2% of gluconate in water.

gluconate-based ointments with suitable excipients.

We claim:

1. An highly water-soluble, antibacterially active salt of 9-fluoro-10-[N-(4''-methyl)piperazinyl]-7-oxo-2,3-dihydro-7H-pyrido[1,2,3,de][1,4]benzothiazine-6-carboxylic acid with an organic acid selected from the group consisting of ethanesulfonic acid, 2-chloroethanesulfonic acid, 2-bromo-ethanesulfonic acid, and gluconic acid.

2. The salt of claim 1, wherein the selected organic salt is ethanesulfonic acid.

3. The salt of claim 1, wherein the selected organic acid is gluconic acid.

4. A therapeutic composition possessing antibacterial activity comprising an effective amount of an highly water-soluble salt of 9-fluoro-10-[N-(4''-methyl)piperazinyl]-7-oxo-2,3-dihydro-7H-pyrido[1,2,3,de][1,4]benzothiazine-6-carboxylic acid with an organic acid selected from the group consisting of ethanesulfonic acid, 2-chloro-ethanesulfonic acid, 2-bromoethanesulfonic acid, and gluconic acid; and a pharmaceutically acceptable diluent or carrier.

5. The therapeutic composition possessing antibacterial activity of claim 4, wherein the selected acid is ethanesulfonic acid.

6. The therapeutic composition possessing antibacterial activity of claim 4, wherein the selected acid is gluconic acid.

* * * * *